US011013394B2

(12) United States Patent
Thornton et al.

(10) Patent No.: US 11,013,394 B2
(45) Date of Patent: May 25, 2021

(54) INSTRUMENT CAP

(71) Applicant: ADVENTIST HEALTH SYSTEM/SUNBELT, INC., Altamonte Springs, FL (US)

(72) Inventors: Jacqueline Thornton, Altamonte Springs, FL (US); Craig Baker, Altamonte Springs, FL (US); Gareth Hearn, Altamonte Springs, FL (US); Jodi Fails, Altamonte Springs, FL (US)

(73) Assignee: ADVENTIST HEALTH SYSTEM/SUNBELT, INC., Altamonte Springs, FL (US)

( * ) Notice: Subject to any disclaimer, the term of this patent is extended or adjusted under 35 U.S.C. 154(b) by 306 days.

(21) Appl. No.: 15/968,310

(22) Filed: May 1, 2018

(65) Prior Publication Data

US 2018/0310807 A1 Nov. 1, 2018

Related U.S. Application Data

(60) Provisional application No. 62/492,537, filed on May 1, 2017.

(51) Int. Cl.
*A61B 1/00* (2006.01)
*G02B 23/24* (2006.01)
*A61B 1/06* (2006.01)

(52) U.S. Cl.
CPC ...... *A61B 1/00137* (2013.01); *A61B 1/00089* (2013.01); *A61B 1/00101* (2013.01); *A61B 1/00144* (2013.01); *A61B 1/00174* (2013.01); *G02B 23/2476* (2013.01); *A61B 1/0014* (2013.01); *A61B 1/0676* (2013.01)

(58) Field of Classification Search
None
See application file for complete search history.

(56) References Cited

U.S. PATENT DOCUMENTS

| 6,457,583 | B1 | 10/2002 | Tee et al. |
| 6,981,945 | B1* | 1/2006 | Sarvazyan ......... A61B 1/00147 600/131 |
| 2007/0212926 | A1 | 9/2007 | Nakaura et al. |
| 2009/0221872 | A1 | 9/2009 | Liddle et al. |
| 2010/0152613 | A1* | 6/2010 | Ryan ..................... A61M 25/00 600/566 |
| 2010/0249510 | A1 | 9/2010 | Yamada |

(Continued)

FOREIGN PATENT DOCUMENTS

| JP | 2007075281 | 3/2007 |
| WO | WO-2016/059383 A2 | 4/2016 |

OTHER PUBLICATIONS

International Search Report from corresponding International Patent Application PCT/US2018/030466 dated Aug. 17, 2018.

(Continued)

*Primary Examiner* — Timothy J Neal
(74) *Attorney, Agent, or Firm* — McCarter & English, LLP (57) ABSTRACT

The present disclosure relates to a cap for protecting an imaging instrument from damage caused by impact or poor handling. Exemplary devices can include a rigid outer shell and soft inner lining surrounding a distal tip of the instrument, to be applied between instrument use, and during instrument transport, disinfection, sterilization, and storage.

7 Claims, 6 Drawing Sheets

(56) References Cited

U.S. PATENT DOCUMENTS

| | | | |
|---|---|---|---|
| 2013/0046138 A1* | 2/2013 | McLawhorn | A61B 1/00101 600/104 |
| 2014/0343361 A1* | 11/2014 | Salman | A61B 1/0014 600/125 |
| 2016/0296105 A1* | 10/2016 | Ramsey | A61B 1/00103 |

OTHER PUBLICATIONS

Ruhof; ScopeValet Tip Guard; https://www.ruhof.com/collections/endoscope-care-products/products/scopevalet-tipguard; Printed May 4, 2017.

* cited by examiner

INSTRUMENT CAP

This application claims priority under 35 U.S.C. § 119 to U.S. Provisional Application No. 62/492,537, which was filed on May 1, 2017. The entire contents of the aforementioned application are incorporated herein by reference in their entirety.

The present disclosure relates generally to caps or covers for protecting endoscopes or similar instruments.

Endoscopy is a medical imaging technique used to image internal organs. Endoscopy is performed using an endoscope, which generally includes a long, flexible shaft fitted at a proximal end with manual controls, and at a distal end with a lens, light, and other imaging apparatuses. Endoscopes are used commonly for procedures such as colonoscopy, laparoscopy, bronchoscopy, esophagogastroduodenoscopy, cystoscopy, endoscopic ultrasound, and the like.

A healthcare professional uses an endoscope by advancing the distal end of the instrument through an opening in the body until an area of interest is reached and visually inspects the area, and optionally performs therapeutic or diagnostic procedures. The instrument's light source and camera illuminate dark regions within the body and allow visualization during the procedure. Visual images are displayed on a monitor to enable the medical professional relative ease of viewing as they guide the instrument through the body cavity. Imaging instruments like endoscopes are powerful diagnostic tools that enable detailed imaging and diagnoses of organs that otherwise may be evaluated using invasive surgical techniques, performed with higher associated risks to a patient.

Although imaging instruments, like endoscopes, have been around since the 1950s, they remain expensive and subject to damage caused from frequent disinfection, sterilization, packaging, and transportation. Delicate electronics, circuitry, and components within or attached to an endoscope, may be particularly sensitive to damage from impact or abrasion. It is beneficial to prevent damage during instances when impact to the endoscope tip is most likely, for example, during removal of the endoscope from the endoscope case and during endoscope disinfection, transport, and storage. Endoscope repair can be expensive and is often performed by sending a damaged device back to the manufacturer—depriving the hospital of that particular device for the duration of the shipping and repair periods, potentially affecting surgery schedules. In order to minimize expenses, and maximize the return on investment of imaging instruments, like endoscopes, it is in the best interest of hospitals to protect imaging instruments, particularly their sensitive distal tips, from damage.

The devices taught herein include caps to protect instrument tips. Protective caps can prevent damage, for example, during transportation, disinfection, sterilization, and storage of endoscopes. Other objects and advantages will be obvious to persons skilled in the art and will in part be apparent from the specification and drawings.

According to certain embodiments, an endoscope protective cap is provided. The cap includes a first component and a second component connected by a hinge, wherein each component comprises a contact surface. The cap is in an open configuration when each contact surface is not in contact with one another and in a closed position when each contact surface is in contact with one another. The cap further includes a first liner positioned within the first component and a second liner positioned with the second component. Each liner includes projections extending radially from an inner surface of each liner to an inner cavity of the cap. The cap further includes a latching mechanism for retaining the first component and the second component in the closed configuration. The cap is configured to receive a distal end of an endoscope in the open configuration and is configured to secure the distal end of an endoscope in a closed configuration.

In some embodiments, at least one of the first component or the second component includes at least one aperture configured to allow the passage of fluid and gas therethrough. At least one of the first liner and the second liner includes at least one aperture positioned above the at least one aperture of at least one of the first component or the second component. The first component and the second component may be composed of polypropylene.

In some embodiments, each contact surface is positioned on opposing ends of the first component and the second component. The projections may be configured to secure narrow portions of the endoscope. The projections may be configured to prevent the endoscope from contacting a distal end of the cap.

In some embodiments, the first liner and the second liner may be composed of cushioning material. The first liner and the second liner may be composed of thermoplastic elastomer.

In some embodiments, the latching mechanism includes a body, a distal tip, a tooth, and an inner face of the second component configured to engage an external face and a catch of the first component. In some embodiments, the hinge may be a living hinge.

In some embodiments, the cap includes alignment marks positioned on a distal portion of the cap. The projections may be positioned distally from the alignment marks. In other embodiments, the projections may be positioned adjacent to the alignment marks.

According to certain embodiments, a method of securing a distal end of an endoscope is provided. The method begins by selecting an endoscope protective cap including a first component and a second component connected by a hinge, wherein each component includes a contact surface. The cap is in an open configuration when each contact surface is not in contact with one another and in a closed position when each contact surface is in contact with one another. The cap further includes a first liner positioned within the first component and a second liner positioned with the second component, each liner including projections extending radially from an inner surface of each liner to an inner cavity of the cap. The cap further includes a latching mechanism for retaining the first component and the second component in the closed configuration. The cap is configured to receive a distal end of an endoscope in the open configuration and is configured to secure the distal end of an endoscope in a closed configuration. Then the distal end of the endoscope is positioned within the first component or the second component and the latching mechanism is closed to secure the distal end of the endoscope within the cap in a closed configuration.

In some embodiments, the endoscope is sterilized and/or high level disinfected. The cap may include at least one aperture configured to allow the free flow of sterilizing agents within the cap. In some embodiments, prior to sterilizing the endoscope the latching mechanism is opened and the endoscope is removed from the first component or the second component and after sterilizing the endoscope the distal end of the endoscope is positioned within the first component or the second component and the latching mechanism is closed to secure the distal end of the endoscope within the cap in a closed configuration.

For a more complete understanding of the invention, it will now be described further by way of example only, and with reference to the following description and accompanying drawings. The drawings are not necessarily to scale.

DESCRIPTION OF CERTAIN EXEMPLARY EMBODIMENTS

Reference will now be made in detail to various embodiments of the disclosed devices and methods of use, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including" as well as other forms, such as "includes" and "included," is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Figure 1A:
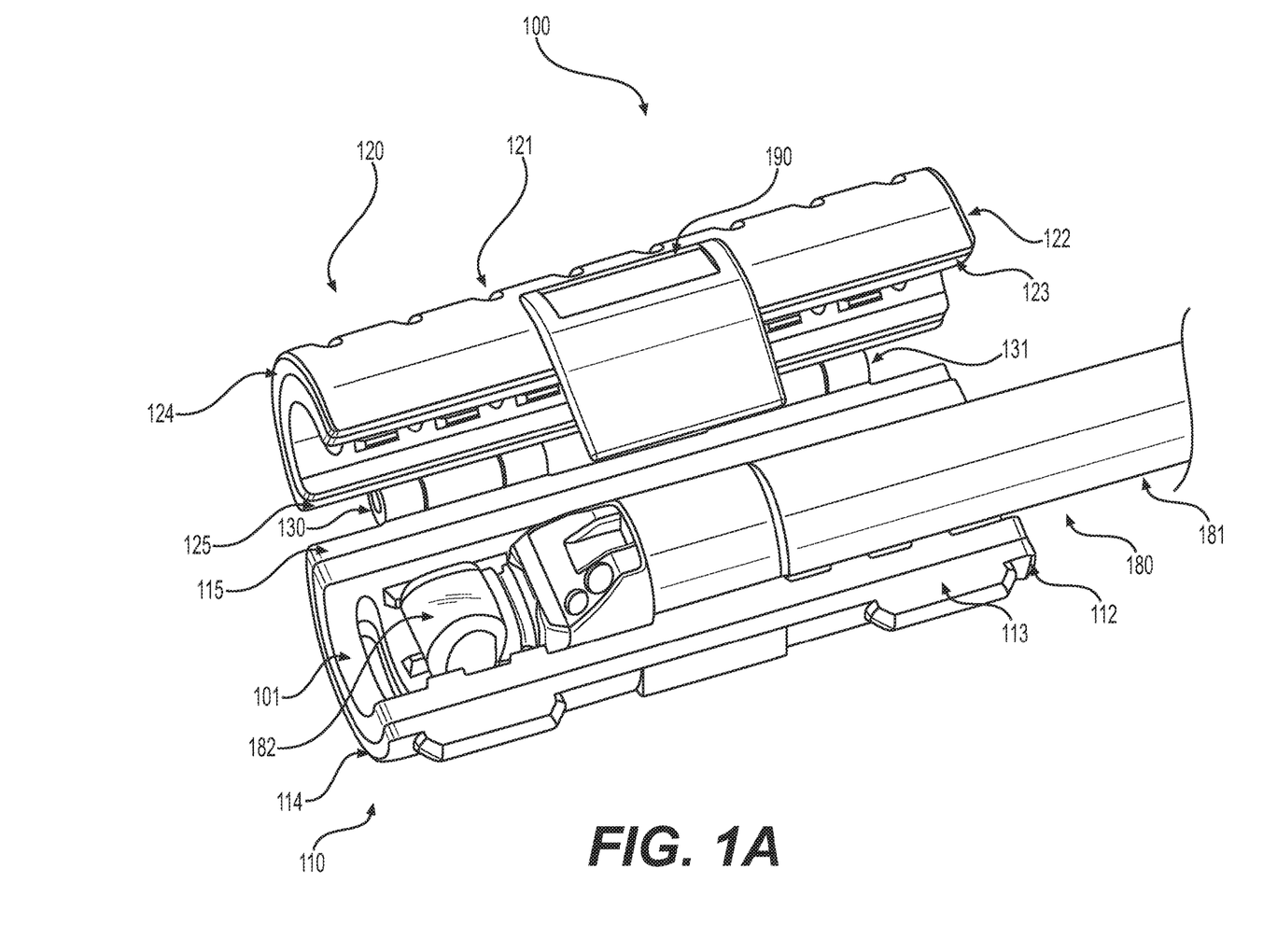
FIG. 1A illustrates a perspective view of one embodiment of a protective cap in an opened position, and a distal tip of an exemplary imaging instrument positioned therein.

Embodiments of the present disclosure relate to a protective cap, alternatively referred to as "cap", that can be mounted on the distal end or tip of an imaging instrument comprising an elongated shaft to protect components such as delicate optical or imaging components. One embodiment of a protective cap 100 is shown in FIG. 1A. The protective cap 100, depicted in an opened configuration with an imaging instrument, such as endoscope 180, disposed therein, can include a first component 110 and a second component 120. Cap 100 may be mounted on the distal tip of exemplary endoscope 180. The various components of the depicted components are described in more detail below.

Figure 2A:
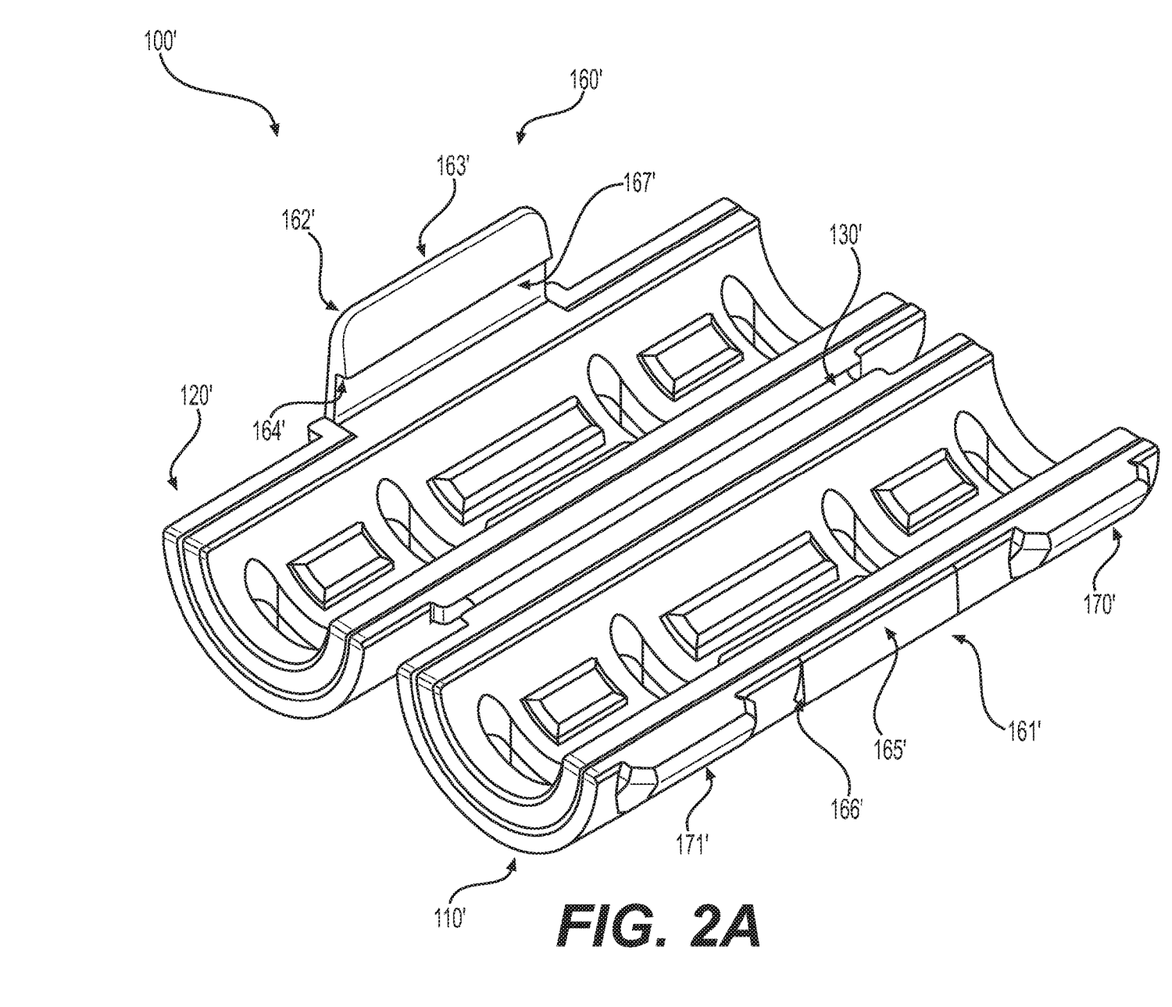
FIG. 2A illustrates a perspective view of one embodiment of a protective cap in an open position.
Figure 2B:
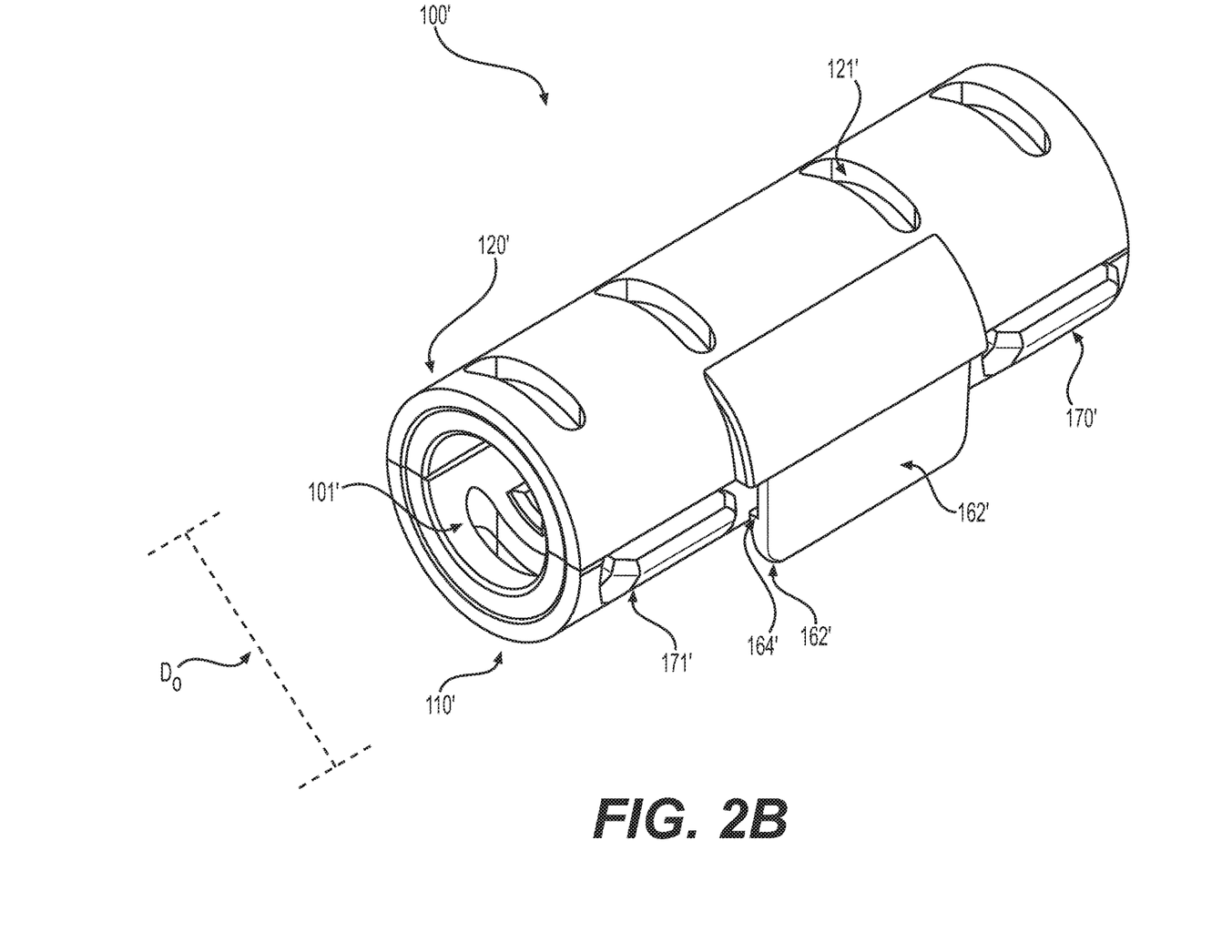
FIG. 2B illustrates a perspective view of one embodiment of a protective cap in a closed position.

Protective cap 100 can be provided in a variety of shapes, including rectangular, spherical, or cylindrical, and may have one axis substantially longer than the remaining two axes, and a characteristic outer diameter $D_o$ (depicted in FIG. 2B). In some embodiments, outer diameter $D_o$ ranges from 5 mm to 20 mm, or any diameter therebetween. Protective cap 100 can include an opening 101 extending partially, or completely, along the long axis of the cap.

Cap 100 may include a first component 110 and a second component 120, which may each additionally include one or more depressions, voids, or apertures 121 through which fluid and gas can pass from outside of cap 100 to the instrument 180 within cap 100, and vice versa. First component 110 and second component 120 may be provided in a variety of shapes, and in one embodiment may each be semi-cylindrical shells with internal semi-circular voids. As shown, the first component 110 and second component 120 each comprise approximately half of the perimeter of cap 100, but one will appreciate that the first component 110 and second component 120 can have different shapes and dimensions. Further, first component 110 and second component 120 may comprise a rigid material suitable for the intended application, such as a polymer, or metal. In some embodiments, first component 110 and second component 120 are comprised of polypropylene. First component 110 may include proximal wall 112 defining, in part, a first end of cap 100. Additionally, first component 110 may include a contact surface 113, and a distal wall 114, the latter defining, in part, a second end of the cap 100.

Second component 120 may include a proximal wall 122 defining, in part, the first end of cap 100. Additionally, second component 120 may include a contact surface 123 and a distal wall 124, the latter defining, in part, the second end of the cap 100. In the closed position of cap 100, first component 110 and second component 120 may be configured such that proximal walls 112 and 122, and distal walls 114 and 124, are aligned with one another, and contact surfaces 113 and 123 contact one another. When cap 100 is in an opened position, first component 110 and second component 120 may be configured such that proximal walls 112 and 122, and distal walls 114 and 124, are aligned with one another, but contact surfaces 113 and 123 do not contact one another. First component 110 and second component 120 may be connected by one or more hinges 130 and 131. The hinges 130 and 131 may be positioned on edges 115 and 125 of first component 110 and second component 120, respectively. In some embodiments, edges 115 and 125 of first component 110 and second component 120 are surfaces running along the length of first component 110 and second component 120.

Figure 1B:
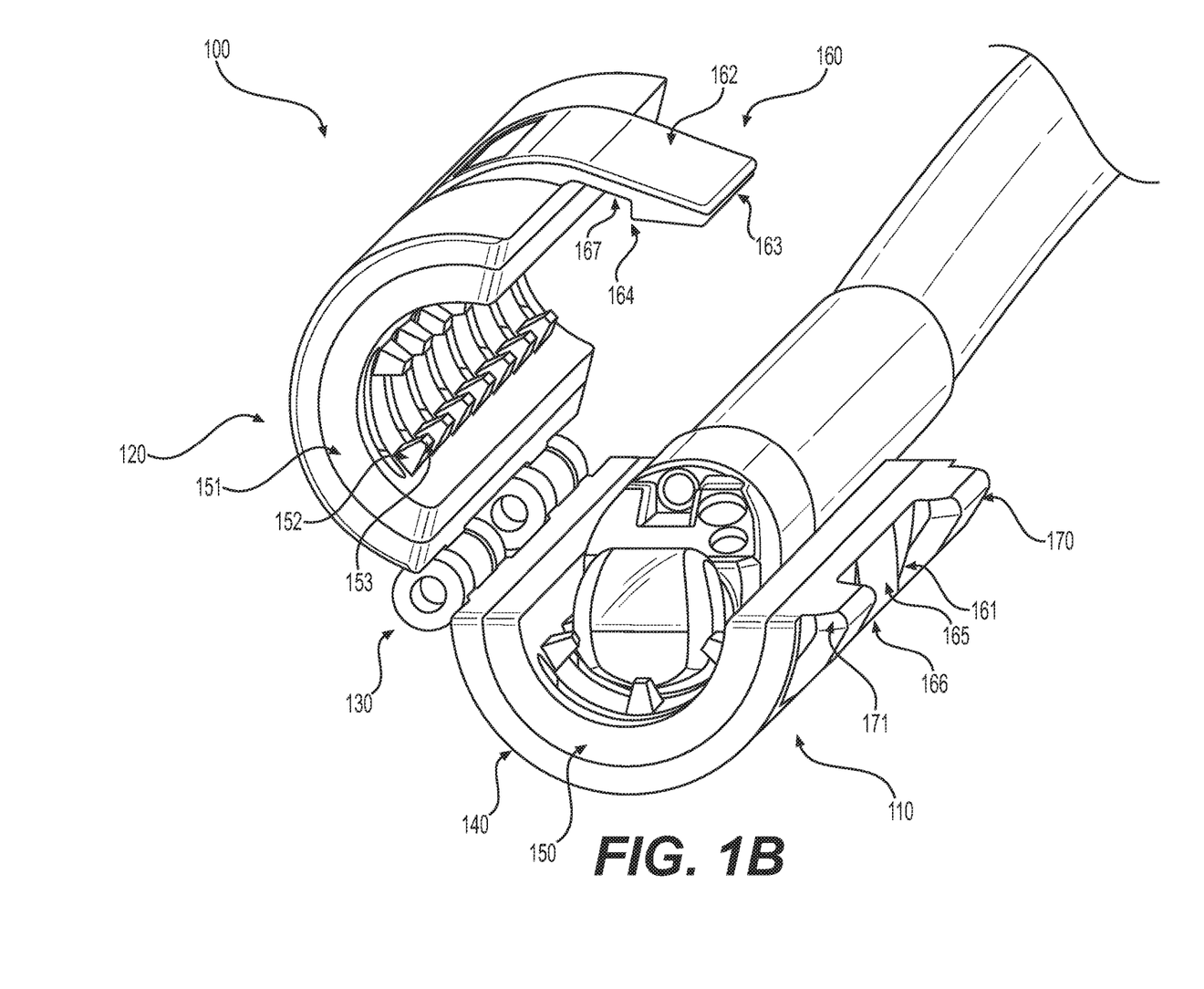
FIG. 1B illustrates an alternate perspective view of one embodiment of a protective cap in an opened position, and a distal tip of an exemplary imaging instrument positioned therein.

First component 110 and second component 120 may include liners 150 and 151, as depicted in FIG. 1B, which may be semi-cylindrical or any other suitable shape. Liner 150 may lie within first component 110, and liner 151 and may lie within second component 120. The liners 150 and 151 may include cushioning material and act as a cushion between the components 110 and 120 and the endoscope 180 to reduce damage to the endoscope 180 if the cap 100 is bumped, dropped, or otherwise disturbed. Apertures 121 in first component 110 and second component 120 may extend through liners 150 and 151, with openings in the exterior, and internal cavity of cap 100. Liners 150 and 151 may include projections 152 that extend from the inner surface of the liner, to the inner cavity of cap 100. Projections 152 may be positioned between apertures 121, and may have a surface 153 that contacts endoscope 180 when cap 100 is in a closed position. Projections 152 may be useful in stabilizing narrow portions of endoscope 180. For example, distal tip 182 of endoscope 180 has a smaller outer diameter than the primary shaft 181. In one embodiment, cap 100 may enclose both distal tip 182 and primary shaft 181. In this configuration, cap 100 may stabilize and protect both sections with the inner surface of liners 150 and 151, and with the surfaces 153 of projections 152. The projections 152 also allow air to flow into the cap 100 during drying and storage to prevent liquid and microorganism buildup. Liners 150 and 151, and projections 152, may be comprised of any number of materials capable of aiding in the protection of the endoscope 180, such as an energy-absorbing material characterized as having a low elastic modulus, or high compliance. In some embodiments, liners 150 and 151 are comprised of thermoplastic elastomer. In some embodiments, the thermoplastic elastomer has a shore value from about 20A to 70A. In further embodiments, the thermoplastic elastomer has a shore value of 43A.

Cap 100 may include a latching mechanism configured to retain first component 110 and second component 120 in a closed position. The latching mechanism may be comprised of a variety of clasping mechanisms. In one embodiment, as depicted in FIG. 1B, a first component of the latching mechanism 160 is a protrusion of second component 120. The first component of the latching mechanism 160 comprises a body 162, distal tip 163, tooth 164, and inner face 167. Body 162 may elastically deform during opening or closing of the cap 100 to disengage from or engage with a second component of the latching mechanism 161. The second component of the latching mechanism 161 may be a protrusion of first component 110, and may comprise an external face 165 and catch 166. As first component 110 and second component 120 are moved from an opened to a closed position, the first component of the latching mechanism 160 approaches the second component of the latching mechanism 161. Tooth 164 passes along the external face 165, until tooth 164 engages catch 166. In the closed configuration, where contact surfaces 113 and 123 contact one another, inner face 167 lies in contact with external face 165, and tooth 164 lies in contact with catch 166. To open cap 100, and pivot second component 120 away from first component 110, the first component of the latching mechanism 160 may be elastically deformed to detach tooth 164 from catch 166, and to separate inner face 167 from external face 165. After this configuration has been achieved, second component 120 may pivot away from first component 110.

In one embodiment, as shown in FIG. 1B, to facilitate manipulation of cap 100, first component 110 may include projections 170 and 171 to allow a user to anchor a counterforce during manipulation of the latching means and to prevent the cap 100 from rolling. Additionally, as depicted in FIG. 1A, second component 120 may include a labelling surface 190 to enable users to mark cap 100 with identifying notation, allowing hospital staff to record traceability history of a single device or otherwise identify devices.

Embodiments in FIGS. 2A and 2B display a cap that is substantially the same as that of FIGS. 1A and 1B, but with variations in the liners and apertures. FIG. 2A displays cap 100' in an open position without an endoscope disposed therein. Cap 100' comprises a first component 110' and second component 120' that may be joined with a hinged connection to enable second component 120' to move with respect to first component 110' to allow opening and closing. Disposed on second component 120' is a first component of the latching mechanism 160'. Disposed on first component 110' is a second component of the latching mechanism 161'. As shown, the first component of the latching mechanism 160' comprises a body 162', distal tip 163', tooth 164', and inner face 167'. Body 162' may elastically deform during opening or closing of the cap 100' to disengage from or align with a second component of the latching mechanism 161'. As first component 110' and second component 120' are moved from an opened to a closed position, the first component of the latching mechanism 160' approaches the second component of the latching mechanism 161'. Tooth 164' passes along the external face 165' until tooth 164' lies in contact with catch 166'. Hinge 130', connecting first component 110' and second component 120', may be a living hinge comprising the same material as first component 110' and second component 120', in a thin and flexible configuration. A living hinge configuration decreases the amount of microorganisms that may get caught in the hinge and be cleaned and disinfected when opened. Further, a cap 100' with a living hinge configuration may be manufactured from a single piece of material and would not require assembly after manufacture.

FIG. 2B depicts cap 100' in a closed position. The first component of the latching mechanism 160' is in contact with the second component of the latching means 161'. Tooth 164' is in contact with catch 166'. Although not visible in FIG. 2B, inner face 167' is in contact with external face 165'. The sizing of cap 100' may be configured so that when the cap 100' is closed using the latching mechanism 160', movement of the cap 100' relative to endoscope 180 is significantly limited. This ensures that the cap 100' does not accidentally become detached from the distal tip 182 of endoscope 180.

Figure 3A:
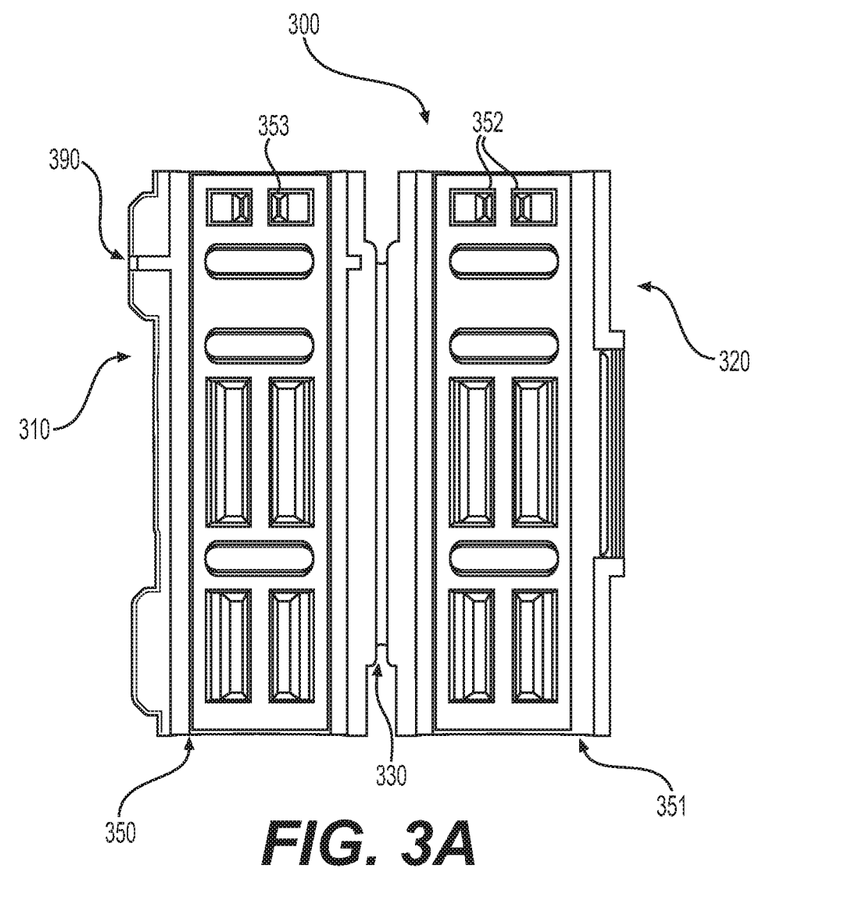
FIG. 3A illustrates a top-down view of one embodiment of a protective cap in an open position.
Figure 3B:
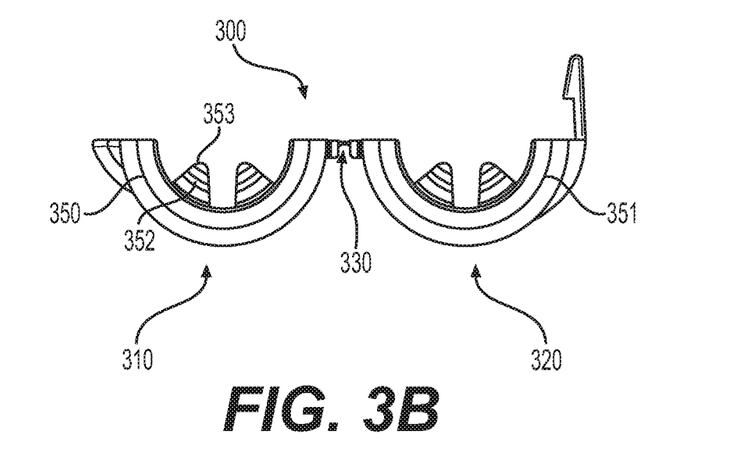
FIG. 3B illustrates a side-end view of one embodiment of a protective cap in an open position.
Figure 3C:
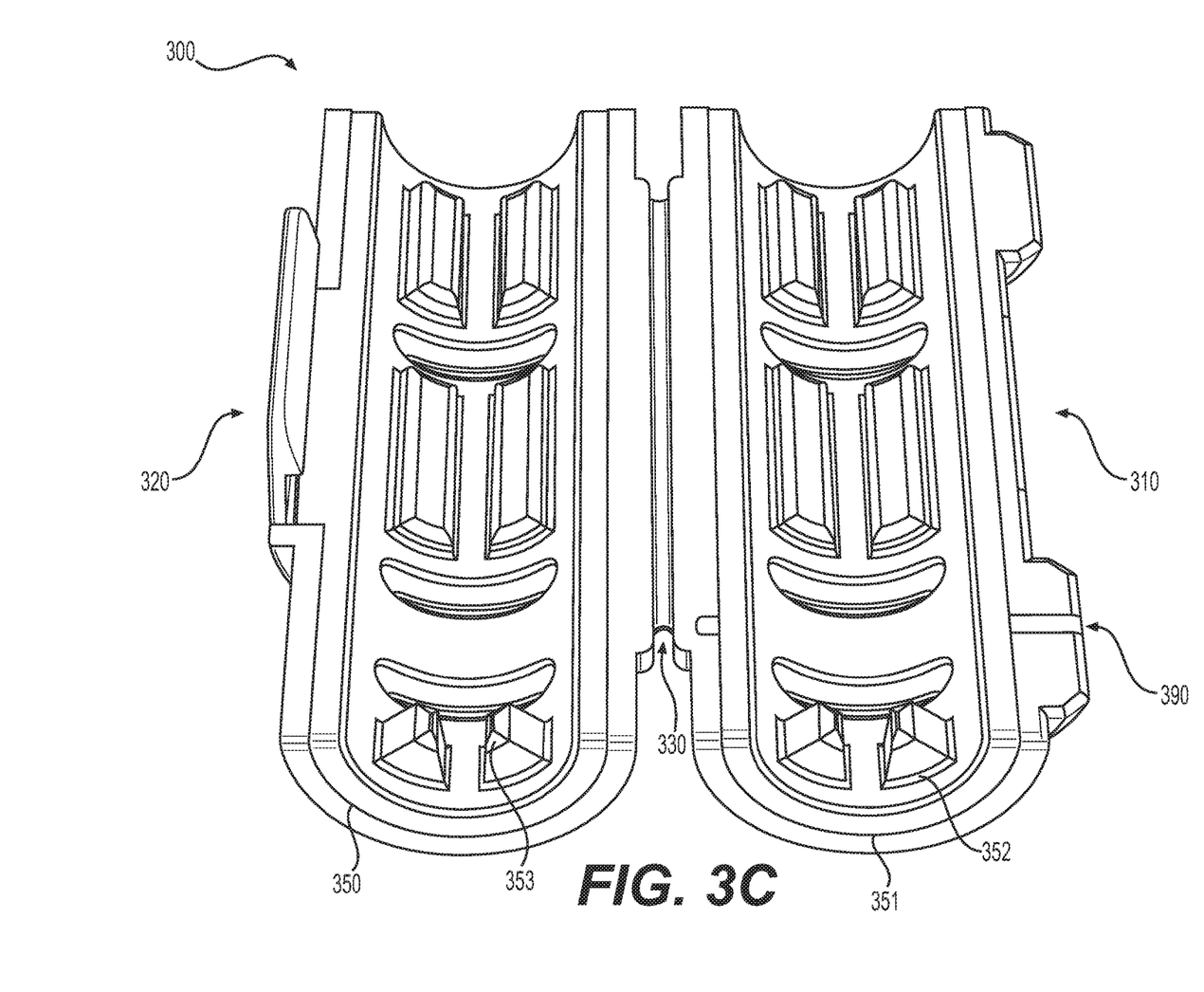
FIG. 3C illustrates a perspective view of one embodiment of a protective cap in an open position.

FIGS. 3A, 3B, and 3C illustrate additional embodiments of the discussed protective caps. Embodiments in FIGS. 3A, 3B, and 3C display a cap 300 that is substantially the same as that of FIGS. 2A and 2B, but include alignment marks and linings of different shapes. Cap 300 includes a first component 310 and second component 320 connected by a hinge 330. Hinge 330 may be a living hinge comprising the same material as first component 310 and second component 320, in a thin and flexible configuration. A living hinge may be continuous material running along a portion of a length of first component 310 and second component 320, enabling movement of first component 310 and second component 320 such that each component can contact on another.

Alignment marks 390 are situated on a distal end of the cap 300 so that a user may identify where to position an endoscope within the cap 300. In some embodiments, the alignment marks 390 are situated on first component 310. In some embodiments, the endoscope is not inserted into the cap 300 beyond the alignment marks 390.

Liners 350 and 351 of cap 300 may include projections 352 at a distal portion of cap 300. Projections 352 may have a surface 353 that contacts endoscope 380 when cap 300 is in a closed position. In some embodiments, the projections 352 may be positioned adjacent to the alignment marks 390. In other embodiments, the projections 352 may be positioned distally from the alignment marks 390. The projections 352 prevent the endoscope from contacting the distal end of the cap 300.

In a clinical setting, after a procedure has been performed, endoscope 180 may be covered by placing endoscope 180 within the internal cavity of cap 100 while cap 100 is in an opened position. Endoscope 180 may be aligned so that the distal tip 182 of endoscope 180 is positioned between the distal walls 114 and 124, and proximal walls 112 and 122. Endoscope 180 may lie in contact with either the inner surface of liners 150 or 151, and with surface 153 of projections 152. A user may adjust cap 100 from an opened to a closed position, engaging tooth 164 with catch 166, thereby retaining cap 100 in a closed position, preventing endoscope 180 from moving relative to the cap 100, and protecting the distal tip of endoscope 180 from potential component damage caused by impact during endoscope transportation, disinfection, sterilization or storage.

Once cap 100 is securely mounted onto the distal tip of endoscope 180 and the endoscope 180 is secured within the cap 100, hospital staff may handle and manipulate the endoscope 180 with a reduced risk of damaging the device, particularly the sensitive optic and lighting components within the distal tip. For example, a secured endoscope 180 may be transported and stored. The secured endoscope 180 may be transported to a location for sterilization.

In some embodiments, an endoscope 180 may be removed from the cap 100 before sterilization and/or high level disinfection. The sterilized endoscope 180 may then be secured within the cap 100 after sterilization is complete. The secured and sterilized endoscope 180 may then be stored before use with another patient. The cap 100 may be sterilized and/or high level disinfected before the sterilized endoscope 180 is secured in the cap 100.

In some embodiments, the endoscope 180 may be sterilized while secured within the cap 100. Apertures 121 within the cap allow for the free flow of sterilizing agents to enter and exit the cap 100. In some embodiments, the endoscope 180 is sterilized while sitting within the cap 100 in an open position. The endoscope 180 may sit within a liner of the cap 100 to prevent damage during handling prior to and after sterilization.

The present disclosure relates to a cap for use with an endoscope. One of skill in the art would appreciate that the cap is suitable for use with additional instruments such as encephaloscopes, laryngoscopes, sophagoscopes, thoracoscopes, angioscopes, nephroscopes, colonoscopes, proctoscopes, arthroscopes, rhinoscopes, esophagoscopes, gastroscopes, and bronchoscopes.

What is claimed is:

1. A method of securing a distal end of an endoscope comprising:
    selecting an endoscope protective cap comprising:
        a first component and a second component connected by a hinge, wherein each component comprises a contact surface and at least one aperture configured to allow the passage of fluid and gas therethrough, the cap being in an open configuration when each contact surface is not in contact with one another and being in a closed configuration when each contact surface is in contact with one another;
        a first liner positioned within the first component and a second liner positioned with the second component, each liner comprising projections extending radially from an inner surface of each liner to an inner cavity of the cap, each liner comprising at least one aperture aligned with the at least one aperture of at least one of the first component or the second component, the at least one aperture of each liner configured to allow the passage of fluid and gas into the cap when the cap is in a closed configuration; and
        a latching mechanism for retaining the first component and the second component in the closed configuration,
        wherein in the open configuration the cap is configured to receive a distal end of an endoscope and in the closed configuration the cap is configured to secure the distal end of an endoscope;
    positioning the distal end of the endoscope within the first component or the second component;
    closing the latching mechanism to secure the distal end of the endoscope within the cap in the closed configuration; and
    sterilizing or disinfecting the distal end of the endoscope within the cap.

2. The method of claim 1, wherein the projections are configured to secure portions of the endoscope narrower in diameter than other portions of the endoscope.

3. The method of claim 1, wherein the projections are configured to prevent the endoscope from contacting a distal end of the cap.

4. The method of claim 1, wherein closing the latching mechanism comprises engaging a tooth of the second component to a catch of the first component.

5. The method of claim 1, wherein the cap further comprises alignment marks positioned on a distal portion of the cap.

6. The method of claim 5, wherein the distal end of the endoscope is positioned adjacent to the alignment marks.

7. The method of claim 1, further comprising:
    prior to sterilizing or disinfecting the distal end of the endoscope and the cap, opening the latching mechanism and removing the endoscope from the first component or the second component; and
    after sterilizing or disinfecting the distal end of the endoscope and the cap, positioning the distal end of the endoscope within the first component or the second component and closing the latching mechanism to secure the distal end of the endoscope within the cap in the closed configuration.

* * * * *